(12) United States Patent
Maher et al.

(10) Patent No.: US 9,418,210 B2
(45) Date of Patent: Aug. 16, 2016

(54) SYSTEMS AND METHODS FOR MANAGING AND PROTECTING ELECTRONIC CONTENT AND APPLICATIONS

(71) Applicant: Intertrust Technologies Corporation, Sunnyvale, CA (US)

(72) Inventors: David P. Maher, Livermore, CA (US); James M. Rudd, San Francisco, CA (US); Eric J. Swenson, Santa Cruz, CA (US); Richard A. Landsman, Scotts Valley, CA (US)

(73) Assignee: Intertrust Technologies Corporation, Sunnyvale, CA (US)

( * ) Notice: Subject to any disclaimer, the term of this patent is extended or adjusted under 35 U.S.C. 154(b) by 0 days.

(21) Appl. No.: 14/571,034

(22) Filed: Dec. 15, 2014

(65) Prior Publication Data

US 2015/0269359 A1 Sep. 24, 2015

Related U.S. Application Data

(63) Continuation of application No. 12/728,098, filed on Mar. 19, 2010, now Pat. No. 8,931,106, which is a (Continued)

(51) Int. Cl.
*H04L 29/06* (2006.01)
*G06F 21/00* (2013.01)
(Continued)

(52) U.S. Cl.
CPC ............... *G06F 21/10* (2013.01); *G06Q 10/10* (2013.01); *G06Q 30/02* (2013.01); *G06Q 50/22* (2013.01); *G06F 2221/0746* (2013.01)

(58) Field of Classification Search
CPC . G06F 21/10; G06F 2221/0746; G06Q 10/10; G06Q 30/02; G06Q 50/22
See application file for complete search history.

(56) References Cited

U.S. PATENT DOCUMENTS

| 4,827,508 A | 5/1989 | Shear |
| 4,924,378 A | 5/1990 | Hershey et al. |

(Continued)

FOREIGN PATENT DOCUMENTS

| EP | 0715247 A1 | 6/1996 |
| WO | WO 96/27155 | 9/1996 |

(Continued)

OTHER PUBLICATIONS http://www.sdmi.org/FAQ.htm (last visit: Mar. 7, 2005).

(Continued)

*Primary Examiner* — Lisa Lewis
(74) *Attorney, Agent, or Firm* — Finnegan, Henderson, Farabow, Garrett & Dunner, LLP

(57) ABSTRACT

Systems and methods are disclosed for managing and protecting electronic content and applications. Applications, content, and/or users can be given credentials by one or more credentialing authorities upon satisfaction of a set of requirements. Rights management software/hardware is used to attach and detect these credentials, and to enforce rules that indicate how content and applications may be used if certain credentials are present or absent. In one embodiment an application may condition access to a piece of electronic content upon the content's possession of a credential from a first entity, while the content may condition access upon the application's possession of a credential from a second entity and/or the user's possession of a credential from a third entity. Use of credentials in this manner enables a wide variety of relatively complex and flexible control arrangements to be put in place and enforced with relatively simple rights management technology.

20 Claims, 10 Drawing Sheets

Related U.S. Application Data continuation of application No. 11/741,556, filed on Apr. 27, 2007, now Pat. No. 7,694,342, which is a continuation of application No. 09/879,743, filed on Jun. 11, 2001, now Pat. No. 7,213,266.

(60) Provisional application No. 60/210,479, filed on Jun. 9, 2000.

(51) Int. Cl.
*G06F 21/10* (2013.01)
*G06Q 10/10* (2012.01)
*G06Q 30/02* (2012.01)
*G06Q 50/22* (2012.01)

(56) References Cited

U.S. PATENT DOCUMENTS

| | | |
|---|---|---|
| 4,977,594 A | 12/1990 | Shear |
| 5,050,213 A | 9/1991 | Shear |
| 5,410,598 A | 4/1995 | Shear |
| 5,530,235 A | 6/1996 | Stefik et al. |
| 5,534,975 A | 7/1996 | Stefik et al. |
| 5,629,980 A | 5/1997 | Stefik et al. |
| 5,634,012 A | 5/1997 | Stefik et al. |
| 5,638,443 A | 6/1997 | Stefik et al. |
| 5,715,403 A | 2/1998 | Stefik |
| 5,892,900 A | 4/1999 | Ginter et al. |
| 5,910,987 A | 6/1999 | Ginter et al. |
| 5,915,019 A | 6/1999 | Ginter et al. |
| 5,917,912 A | 6/1999 | Ginter et al. |
| 5,920,861 A | 7/1999 | Hall et al. |
| 5,925,127 A | 7/1999 | Ahmad |
| 5,940,504 A | 8/1999 | Griswold |
| 5,943,422 A | 8/1999 | Van Wie et al. |
| 5,949,876 A | 9/1999 | Ginter et al. |
| 5,982,891 A | 11/1999 | Ginter et al. |
| 5,982,898 A | 11/1999 | Hsu et al. |
| 5,999,949 A | 12/1999 | Crandall |
| 6,112,181 A | 8/2000 | Shear et al. |
| 6,138,119 A | 10/2000 | Hall et al. |
| 6,157,721 A | 12/2000 | Shear et al. |
| 6,185,683 B1 | 2/2001 | Ginter et al. |
| 6,189,097 B1 | 2/2001 | Tycksen, Jr. et al. |
| 6,237,786 B1 | 5/2001 | Ginter et al. |
| 6,240,185 B1 | 5/2001 | Van Wie et al. |
| 6,253,193 B1 | 6/2001 | Ginter et al. |
| 6,260,043 B1 | 7/2001 | Puri et al. |
| 6,292,569 B1 | 9/2001 | Shear et al. |
| 6,330,491 B1 | 12/2001 | Lion |
| 6,363,488 B1 | 3/2002 | Ginter et al. |
| 6,389,402 B1 | 5/2002 | Ginter et al. |
| 6,427,140 B1 | 7/2002 | Ginter et al. |
| 6,449,367 B2 | 9/2002 | Van Wie et al. |
| 6,453,418 B1 | 9/2002 | Ooki et al. |
| 6,618,484 B1 | 9/2003 | Van Wie et al. |
| 6,640,304 B2 | 10/2003 | Ginter et al. |
| 6,658,568 B1 | 12/2003 | Ginter et al. |
| 6,662,365 B1 | 12/2003 | Sullivan et al. |
| 6,668,325 B1 | 12/2003 | Collberg et al. |
| 6,775,655 B1 | 8/2004 | Peinado et al. |
| 6,785,815 B1 | 8/2004 | Serret-Avila et al. |
| 6,820,063 B1 | 11/2004 | England et al. |
| 6,832,316 B1 | 12/2004 | Sibert |
| 7,114,075 B1 | 9/2006 | Yasuda et al. |
| 8,843,997 B1 * | 9/2014 | Hare .................. H04L 63/0281 709/200 |
| 8,863,252 B1 * | 10/2014 | Katzer .................. G06F 21/53 705/71 |
| 2001/0042043 A1 | 11/2001 | Shear et al. |
| 2002/0023214 A1 | 2/2002 | Shear et al. |
| 2002/0048369 A1 | 4/2002 | Ginter et al. |
| 2002/0087859 A1 | 7/2002 | Weeks et al. |
| 2002/0112171 A1 | 8/2002 | Ginter et al. |
| 2002/0152173 A1 | 10/2002 | Rudd |
| 2003/0023856 A1 | 1/2003 | Horne et al. |
| 2003/0041239 A1 | 2/2003 | Shear et al. |
| 2003/0046244 A1 | 3/2003 | Shear et al. |
| 2003/0069748 A1 | 4/2003 | Shear et al. |
| 2003/0069749 A1 | 4/2003 | Shear et al. |
| 2003/0084003 A1 | 5/2003 | Pinkas et al. |
| 2003/0105721 A1 | 6/2003 | Ginter et al. |
| 2003/0163431 A1 | 8/2003 | Ginter et al. |
| 2004/0054630 A1 | 3/2004 | Ginter et al. |
| 2004/0059951 A1 | 3/2004 | Pinkas et al. |
| 2004/0073813 A1 | 4/2004 | Pinkas et al. |
| 2004/0103305 A1 | 5/2004 | Ginter et al. |
| 2004/0107356 A1 | 6/2004 | Shamoon et al. |
| 2004/0123129 A1 | 6/2004 | Ginter et al. |
| 2004/0133793 A1 | 7/2004 | Ginter et al. |
| 2004/0250060 A1 * | 12/2004 | Diep .................. G06F 9/548 713/155 |
| 2005/0027871 A1 | 2/2005 | Bradley et al. |
| 2005/0050332 A1 | 3/2005 | Serret-Avila et al. |
| 2005/0060560 A1 | 3/2005 | Sibert |
| 2005/0060584 A1 | 3/2005 | Ginter et al. |
| 2005/0108555 A1 | 5/2005 | Sibert |

FOREIGN PATENT DOCUMENTS

| | | |
|---|---|---|
| WO | WO 98/09209 | 3/1998 |
| WO | WO 98/37481 | 8/1998 |
| WO | WO 99/01815 | 1/1999 |
| WO | WO 99/24928 | 5/1999 |
| WO | WO 99/48296 | 9/1999 |
| WO | WO 00/75925 | 12/2000 |
| WO | WO 01/09702 | 2/2001 |

OTHER PUBLICATIONS http://www.sdmi.org/who_we_are.htm (last visit: Mar. 7, 2004).

Menezes, A. J. et al., Handbook of Applied Cryptography, CRC Press, Oct. 1996. ISBN 0-8493-8523-7 (hardcover).

Schneier, B., Applied Cryptography, 2d ed., John Wiley & Sons, Oct. 1995. ISBN 0-4711-1709-9 (paperback).

Sibert, Olin, et al., "DigiBox: A Self-Protecting Container for Information Commerce," Proceedings of the First USENIX Workshop on Electronic Commerce, New York, NY, Jul. 1995, pp. 1-9.

Sibert, Olin, et al., "Securing the Content, Not the Wire, for Information Commerce," InterTrust Technologies Corporation, 1996, pp. 1-12.

Stefik, M., "Chapter 7, Classification, Introduction to Knowledge Systems," Morgan Kaufmann Publishers, Inc., 1995, pp. 543-607.

Stefik, M., "Letting Loose the Light: Igniting Commerce in Electronic Publication," Internet Dreams: Archetypes, Myths, and Metaphors. Massachusetts Institute of Technology, 1996, pp. 219-253.

Stefik, M., "Letting Loose the Light: Igniting Commerce in Electronic Publication," Xerox PARC, Palo Alto, CA, 1994-1995, pp. 1-35.

Stefik, M., "Trusted Systems," Scientific American, Mar. 1997, pp. 78-81.

Unknown, "SDMI Portable Device Specification, part 1, Version 1.0", Jun. 8, 1999.

Office Action mailed Mar. 21, 2005, in U.S. Appl. No. 09/879,743, filed Jun. 11, 2001.

Final Office Action mailed Dec. 8, 2005, in U.S. Appl. No. 09/879,743, filed Jun. 11, 2001.

Office Action mailed Aug. 22, 2006, in U.S. Appl. No. 09/879,743, filed Jun. 11, 2001.

Notice of Allowance mailed on Mar. 7, 2007, in U.S. Appl. No. 09/879,743, filed Jun. 11, 2001.

Office Action mailed Apr. 30, 2009, in U.S. Appl. No. 11/741,556, filed Apr. 27, 2007.

Notice of Allowance mailed Nov. 17, 2009, in U.S. Appl. No. 11/741,556, filed Apr. 27, 2007.

Office Action mailed Nov. 29, 2011, in U.S. Appl. No. 12/728,098, filed Mar. 19, 2010.

(56) References Cited

OTHER PUBLICATIONS

Office Action mailed Apr. 13, 2012, in U.S. Appl. No. 12/728,098, filed Mar. 19, 2010.
Office Action mailed May 23, 2013, in U.S. Appl. No. 12/728,098, filed Mar. 19, 2010.
Office Action mailed Apr. 28, 2014 in U.S. Appl. No. 12/728,098 filed Mar. 19, 2010.
Notice of Allowance mailed Sep. 4, 2014, in U.S. Appl. No. 12/728,098, filed Mar. 19, 2010.

* cited by examiner

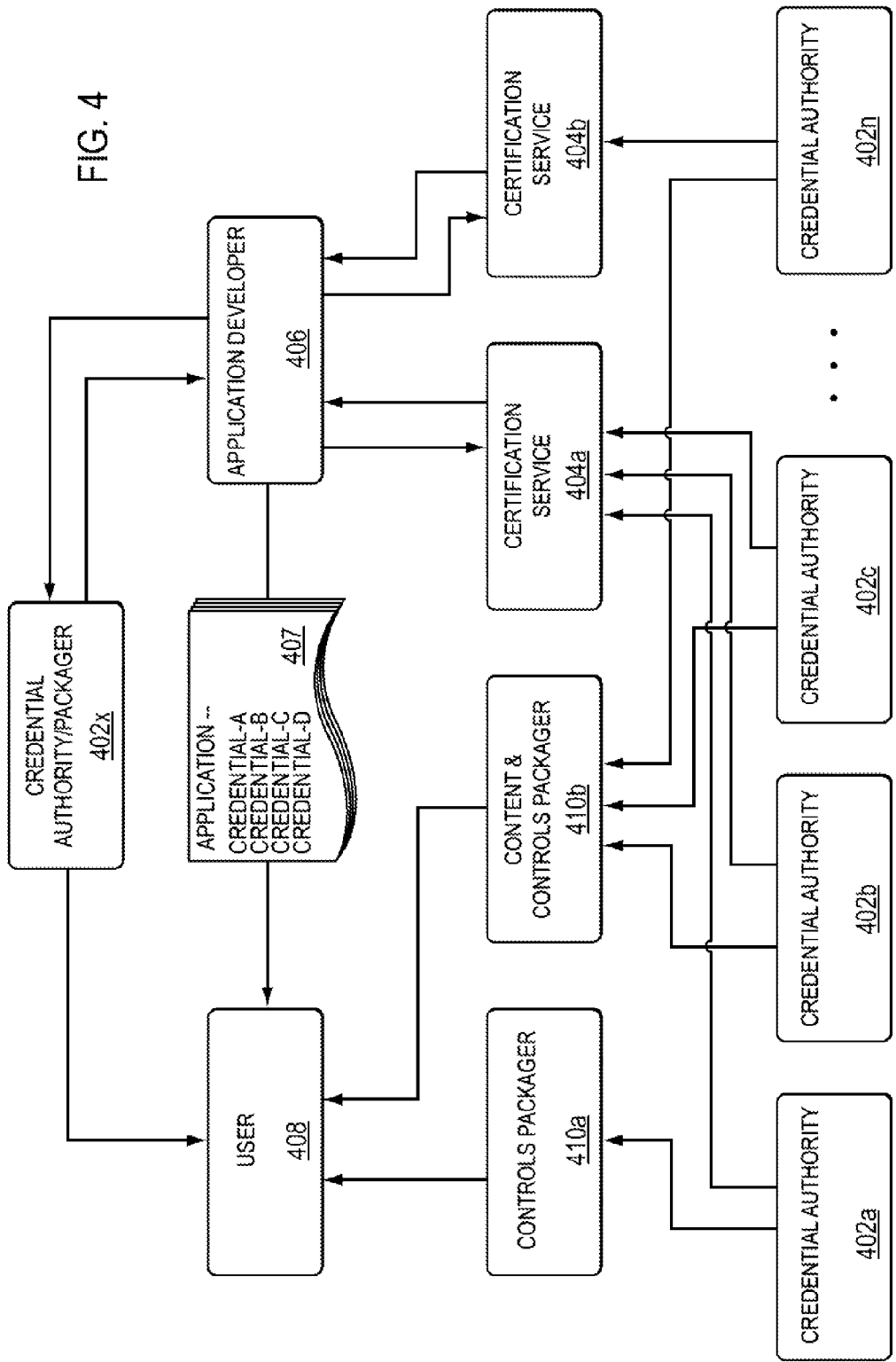

DRM SYSTEM CREDENTIAL -- 802

Signature -- 804

Tamper Resistance: High -- 806

Host Platform: OS-version -- 808

APPLICATION CREDENTIAL -- 812

Signature -- 814

Content Exposure: Moderate -- 816

Output Driver: Direct Check -- 818

FIG. 8

SYSTEMS AND METHODS FOR MANAGING AND PROTECTING ELECTRONIC CONTENT AND APPLICATIONS

RELATED APPLICATIONS

This is a continuation of application Ser. No. 12/728,098, filed Mar. 19, 2010, which is a continuation of application Ser. No. 11/741,556, filed Apr. 27, 2007, now U.S. Pat. No. 7,694,342 issued Apr. 6, 2010, which is a continuation of application Ser. No. 09/879,743, filed Jun. 11, 2001, now U.S. Pat. No. 7,213,266 issued May 1, 2007, which claims the benefit of U.S. Provisional Application No. 60/210,479, filed Jun. 9, 2000, each of which are incorporated herein by reference.

COPYRIGHT AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to managing electronic content. More specifically, systems and methods are disclosed for governing electronic content and applications through the use of electronic credentials and certification procedures.

BACKGROUND OF THE INVENTION

With the advent of the Internet and the prevalent use of electronic systems, increased attention has been paid to protecting the interests of content owners and to ensuring that the integrity of electronic transactions is not compromised. These are difficult tasks, however, as the differences between electronic systems and their physical counterparts can have a profound effect on the feasibility of such protections and the ease with which they can be implemented.

While increasing attention has been paid to the development of systems that address these problems, these systems often lack interoperability with other such systems, are overly complex, and/or place an unduly large burden on a relatively small number of entities to provide the bulk of the system's security and functionality.

Systems and methods are thus needed for providing content creators, application developers, consumers, and regulators with increased power and flexibility to define and create efficient markets for the exchange, control, and protection of digital goods and for the performance of electronic transactions.

SUMMARY OF THE INVENTION

The present invention provides systems and methods for managing electronic content, and for enabling content owners, regulators, and others to create flexible controls for content and applications and to manage their level of risk. It should be appreciated that the present invention can be implemented in numerous ways, including as a process, an apparatus, a system, a device, a method, a computer readable medium, or as a combination thereof. Several inventive embodiments are described below.

A method for certifying the functionality of an application program is disclosed. The method includes sending an issuer's credential to a certification service, the credential being associated with at least (i) a set of rules that govern the use of the credential and (ii) a set of certification requirements. The method further includes sending an application to the certification service and verifying that the application meets the certification requirements. If the application meets the certification requirements, a credential is attached to the application in a manner designed to facilitate detection of modifications to the application that would affect the application's compliance with the certification requirements. A digital rights management engine obtains content with an associated control that indicates that the content is to be used only on applications that include a certain credential. The digital content may also be associated with a credential that indicates that it meets certain criteria. When an application attempts to access the content, the digital rights management engine checks the application for the appropriate credential. If the credential is found, the digital rights management engine may allow the content to be used by the application; otherwise, the digital rights management engine denies access to the content. The application may check the content for the content's credential, and refuse to process the content if the credential is not present or has been revoked.

In another embodiment, a method of controlling the use of electronic content and applications is disclosed. The method includes associating a plurality of credentials with an application, each credential demonstrating the application's compliance with a predefined specification. A piece of content is associated with a control set that checks applications for the presence of one or more credentials. The control set is operable to allow use of the content if the appropriate credentials are detected. In one embodiment, pieces of electronic content are also associated with one or more credentials, and an application is associated with a control set that is operable to cause a check to be made of the credentials held by a piece of electronic content. If the appropriate credentials are detected, then the application processes the electronic content.

These and other features and advantages of the present invention will be presented in more detail in the following detailed description and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which:

FIG. 4 illustrates a system for certifying and credentialing applications in accordance with an embodiment of the present invention.

FIG. 8 illustrates credentials with multiple attributes.

DETAILED DESCRIPTION

A detailed description of the invention is provided below. While the invention is described in conjunction with several embodiments, it should be understood that the invention is not limited to any one embodiment. On the contrary, the scope of the invention is limited only by the appended claims and encompasses numerous alternatives, modifications, and equivalents. In addition, while numerous specific details are set forth in the following description in order to provide a thorough understanding of the present invention, the present invention may be practiced according to the claims without some or all of these details. For the purpose of clarity, certain technical material that is known in the art has not been described in detail in order to avoid obscuring the present invention. For example, reference will be made to a number of terms and concepts that are well-known in the field of cryptography. Background information on cryptography can be found, for example, in Menezes et al., *Handbook of Applied Cryptography* (CRC Press 1996)("Menezes"); and Schneier, *Applied Cryptography*, 2d ed. (John Wiley & Sons 1995).

The present invention provides systems and methods for enhancing the flexibility, efficiency, and interoperability of digital rights management systems. Specifically, in one embodiment systems and methods are provided for enabling a wide range of disparate entities to certify applications, content, and/or users, and to provide application developers, content packagers, users, regulatory bodies, and/or system administrators with a way to condition content access and/or use on the detection of one or more credentials associated with the outcome of the certification process. Thus, the systems and methods of the present invention can be used to reduce the burden placed on any given certification service, since a single authority is not needed to perform a full certification of all applications, content, users, and the like. The systems and methods of the present invention also enable the efficient and flexible association of precisely-tailored rules with content via the application-certification and user-certification processes, thus enabling rights management systems to be implemented more efficiently and/or compactly.

Figure 1:
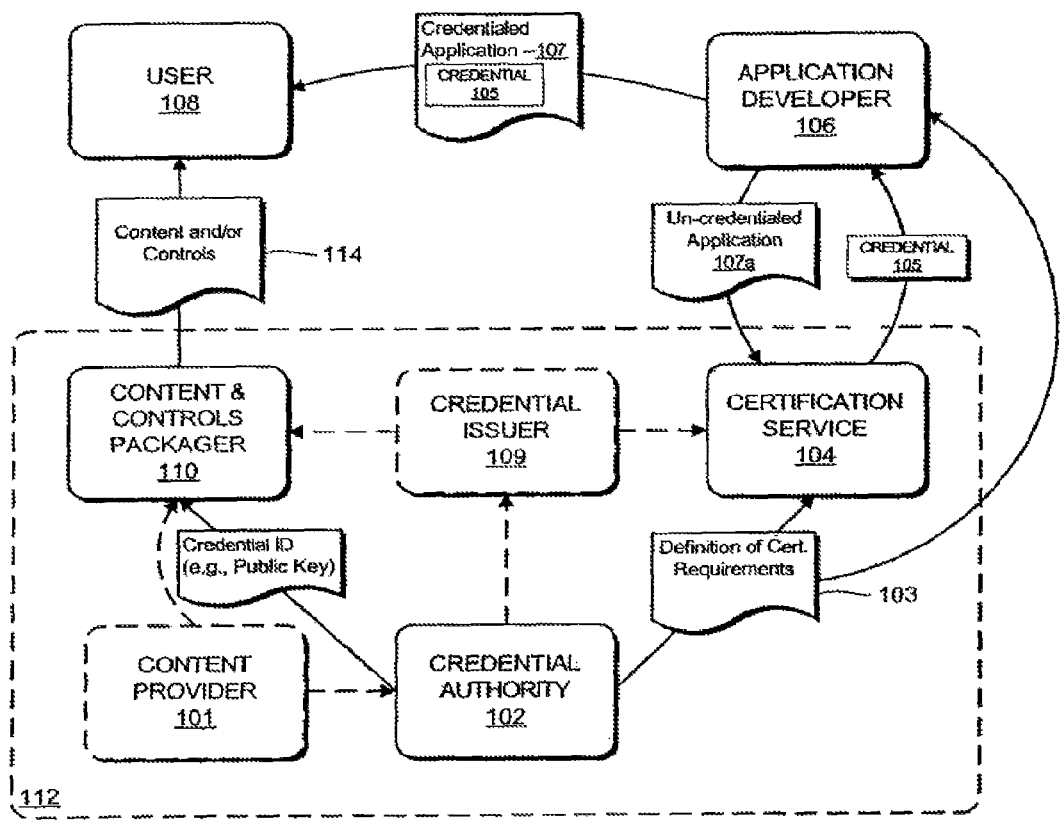
FIG. 1 illustrates a system for certifying and credentialing applications in accordance with an embodiment of the present invention.

FIG. 1 illustrates a system for practicing an embodiment of the present invention. Referring to FIG. 1, a credential authority 102 defines a set of requirements 103 that applications must meet in order to receive the authority's credential. Credential authority 102 may, for example, represent a content provider, an industry association of content providers, a governmental or regulatory body, a consumer protection organization, a network security firm, a digital rights management provider, or any other suitable entity with an interest in controlling certain aspects of the use or exchange of electronic information. Requirements 103 may, for example, specify the way an application 107 is supposed to handle or present electronic content to user 108.

As shown in FIG. 1, in some embodiments credential authority 102 supplies its certification requirements 103 to an application developer 106 and a certification service 104. Application developer 106 creates an application 107a that conforms to requirements 103 and provides it to certification service 104. Certification service analyzes and tests application 107a to make sure that it meets the requirements 103 specified by credential authority 102. An application 107a that satisfies these requirements is given an appropriate credential or certificate 105. Upon obtaining credential 105, the application developer 106 may distribute the credentialed application 107 to an application user 108.

Credential authority 102 also issues a copy of its credential ID and/or related identification data (e.g., one of the credential authority's public keys, or a public key of the entity from which authorization must ultimately flow) to content and controls packager 110. Content and controls packager 110 takes the credential ID or related data and uses it to create controls that can be associated with the content provider's content, the controls being operable to trigger a test for the credential before allowing certain uses of the content. In a preferred embodiment these controls can be updated and delivered remotely and/or independently of the content. Additional information on the creation of rules and controls and on the association of rules and controls with content can be found in commonly-assigned U.S. Pat. No. 5,892,900, entitled "Systems and Methods for Secure Transaction Management and Electronic Rights Protection," issued Apr. 6, 1999 ("the '900 patent"), which is hereby incorporated by reference in its entirety.

When user 108 attempts to use application 107 to process content 114, the user's system checks application 107 for the presence of the appropriate credential 105. If the credential 105 is present, the application 107 may proceed with using content 114. If credential 105 is not present, use of content 114 can be prohibited. Thus, when the credential 105 of an authority 102 is securely associated with an application 107—and content 114 is associated with a rule requiring credential 105 to be present as a condition of granting application 107 access to the content—application users 108 and content providers 101 can be confident, within the security bounds of the certification process and/or the credential, that the application will operate in accordance with the credential authority's requirements and specifications.

It will be appreciated that there are numerous ways to implement the functionality illustrated in FIG. 1. For example, in some embodiments content and controls packager 110 may comprise one or more distinct entities which package content and/or provide rules and controls that can be associated with previously-packaged content. In other embodiments credential authority 102 may perform the functions of content and controls packager 110 and/or certification service 104 itself, as indicated in FIG. 1 by dotted line 112. Similarly, in some embodiments a credential issuer/provider 109 is used to generate the appropriate credentials, to affix these credentials to application 107a, and to provide identification information to packager 110 for use in creating rules that identify these credentials. In other embodiments, the functionality of credential issuer 109 can be subsumed within that of any suitable combination of one or more of the other entities shown in FIG. 1. For example, the content owner and/or credential authority may generate the appropriate credential and/or affix it to the application or content.

Figure 2:
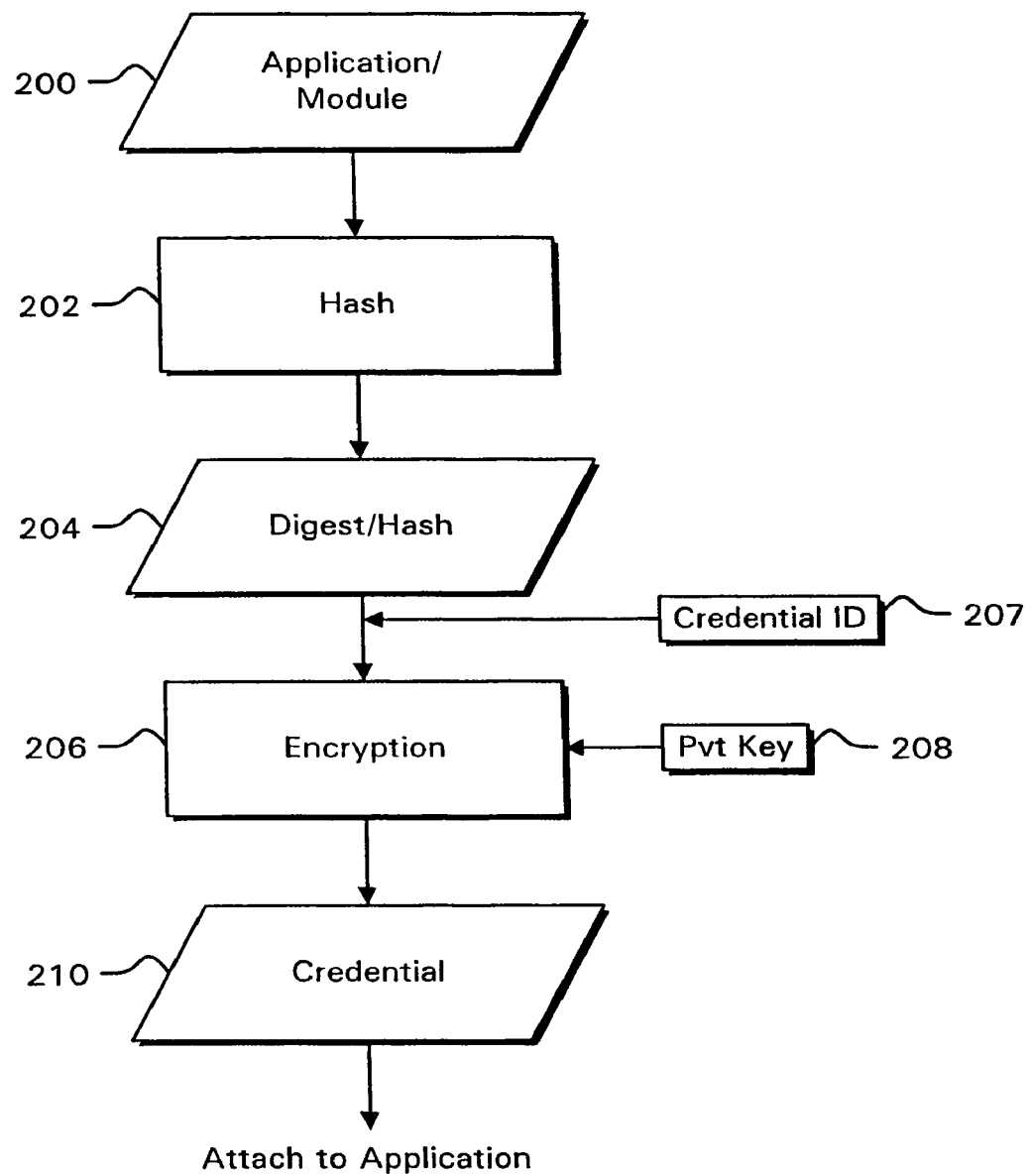
FIG. 2 illustrates the generation of an application credential.

Well-known cryptographic techniques can be used to generate credentials 105. For example, as shown in FIG. 2, in some embodiments credential 105 is formed by applying a strong cryptographic hash algorithm (e.g., SHA-1) 202 to the application 200 (or to selected portions thereof) to yield hash or message digest 204. Message digest 204 (and, in some embodiments, identification information 207) is encrypted (206) using the certification service's (or credential authority's) private key 208 to yield credential or signature 210. One of ordinary skill in the art will recognize that a number of variations could be made to the process shown in FIG. 2. For example, in some embodiments, a checksum of all or part of the application could be used instead of, or in addition to, the hash or message digest 204. It will be appreciated that there are a variety of other techniques for generating a credential or certificate for an application, and that for purposes of practicing the present invention any suitable technique can be used. For example, use could be made of the techniques described in Menezes at pages 1-45 and 283-488, the '900 patent, commonly-assigned U.S. Pat. No. 6,157,721, entitled "Systems and Methods Using Cryptography to Protect Secure Computing Environments," issued Dec. 5, 2000 ("the '721 patent"), commonly-assigned U.S. patent application Ser. No. 09/628,692, entitled "Systems and Methods for Using Cryptography to Protect Secure and Insecure Computing Environments," and commonly-assigned U.S. patent application Ser. No. 09/863,199, entitled "Trust Management Systems and Methods," filed May 21, 2001, each of which is hereby incorporated by reference in its entirety. In other embodiments, the use of a special certificate or credential (it should be noted that, in general, these two terms will be used interchangeably) could be dispensed with, and verification of the certification or authorization of an application, user, or content object could simply be inferred based on possession of a cryptographic key (e.g., a private or secret key) and/or other secret (or not so secret) information.

In some embodiments the user's system 108 includes digital rights management hardware and/or software for managing protected content and for enforcing the rules and controls associated therewith. For example, INTERRIGHTS POINT™ software or RIGHTS/SYSTEM™ software could be used, as could the Rights Operating System software described in the '900 patent or other systems that implement some or all of the virtual distribution environment functionality described therein. Alternatively, other digital rights management hardware and/or software could be used. Use of digital rights management software/hardware may be helpful in situations where the user may not be trusted and/or where the user's system may be deemed to be otherwise insufficiently secure or reliable. As explained in the '900 patent, digital rights management software/hardware can be used to ensure the secure, confidential, and reliable performance of important operations, such as enforcing the rules associated with content (e.g., making sure that a credential check is performed, and that it is performed accurately).

In preferred embodiments, communications between the user 108 and the content provider 101 and/or content packager 110 are conducted via secure containers (e.g., encrypted electronic files). For example, DIGIBOX® or DIGIFILE™ secure containers produced by Intertrust Technologies Corporation of 955 Stewart Drive, Sunnyvale, Calif. could be used. When a user attempts to access content contained in a secure container, the user's application sends the content to the digital rights management system which extracts the content and/or the rules associated with the content, evaluates the rules, and determines whether the application is allowed to access the content and on what terms access should occur. For example, the digital rights management system preferably handles the credential-verification process described above, and releases content to a rendering application only if the appropriate credential is found and verified.

By using the certificates in this manner, content owners are effectively able to condition the use of their content on certain characteristics of the content-rendering application without the necessity of explicitly including the details of these requirements in the controls that are directly associated with the content. For example, if the content owner wanted to ensure that the content was used in a very specific manner by a rendering application, this could be handled by a single certificate, rather than requiring the digital rights management system to be modified or enhanced to allow these particular rules to be expressed, associated with the content item, interpreted by the digital rights management system, and carried out by the application (which would typically need to be certified by the digital rights management provider to ensure that the application would behave in a manner that was consistent with the rules). Thus, the present invention can help reduce the complexity of digital rights management systems and the burden placed on the provider of the digital rights management system to ensure interoperability with other applications.

Figure 3A:
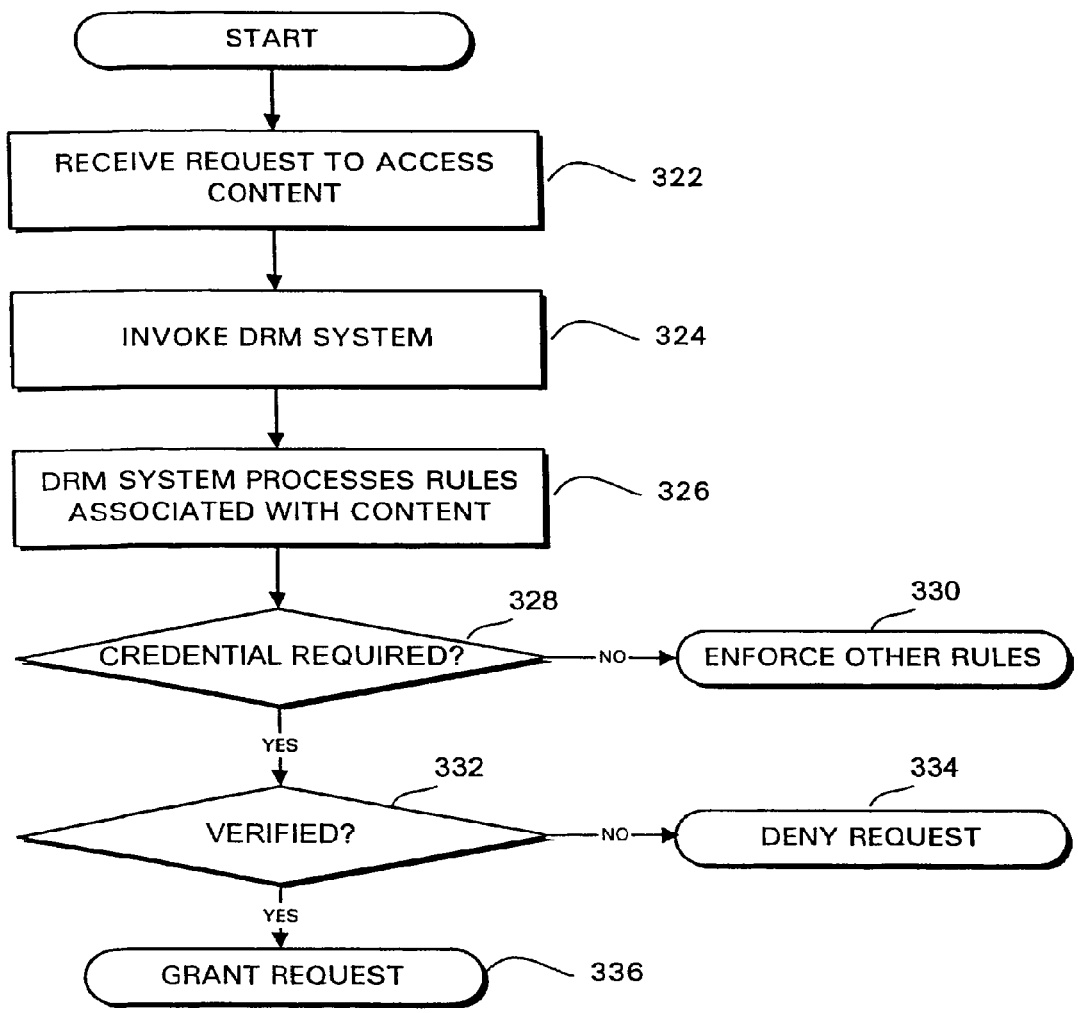
FIGS. 3A and 3B illustrate the verification of an application credential.

FIG. 3A illustrates the steps a user's system might perform in order to determine if a requested piece of content can be accessed. Referring to FIG. 3A, upon receiving a request to access a piece of content (322), the rendering application (and/or the operating system of the user's system, via MIME type mapping) invokes the rights management software/hardware that is operable to decide whether to grant or deny access to the content (324). The rights management system will typically base its decision on rules associated with the content, rendering application, user, and/or system. As described in the '900 patent, these rules may, for example, be stored in a protected database or encrypted with the content. The digital rights management hardware/software determines which, if any, rules are relevant to the user's request (326), and, if one of the rules indicates that a certain credential is required, the digital rights management system checks for this credential (328). For example, the digital rights management system may examine a predefined portion of the application, or may simply send the application a request for the credential. If the credential is verified, the digital rights management system releases the content for the requested use (336); otherwise, the request is denied (334).

Figure 3B:
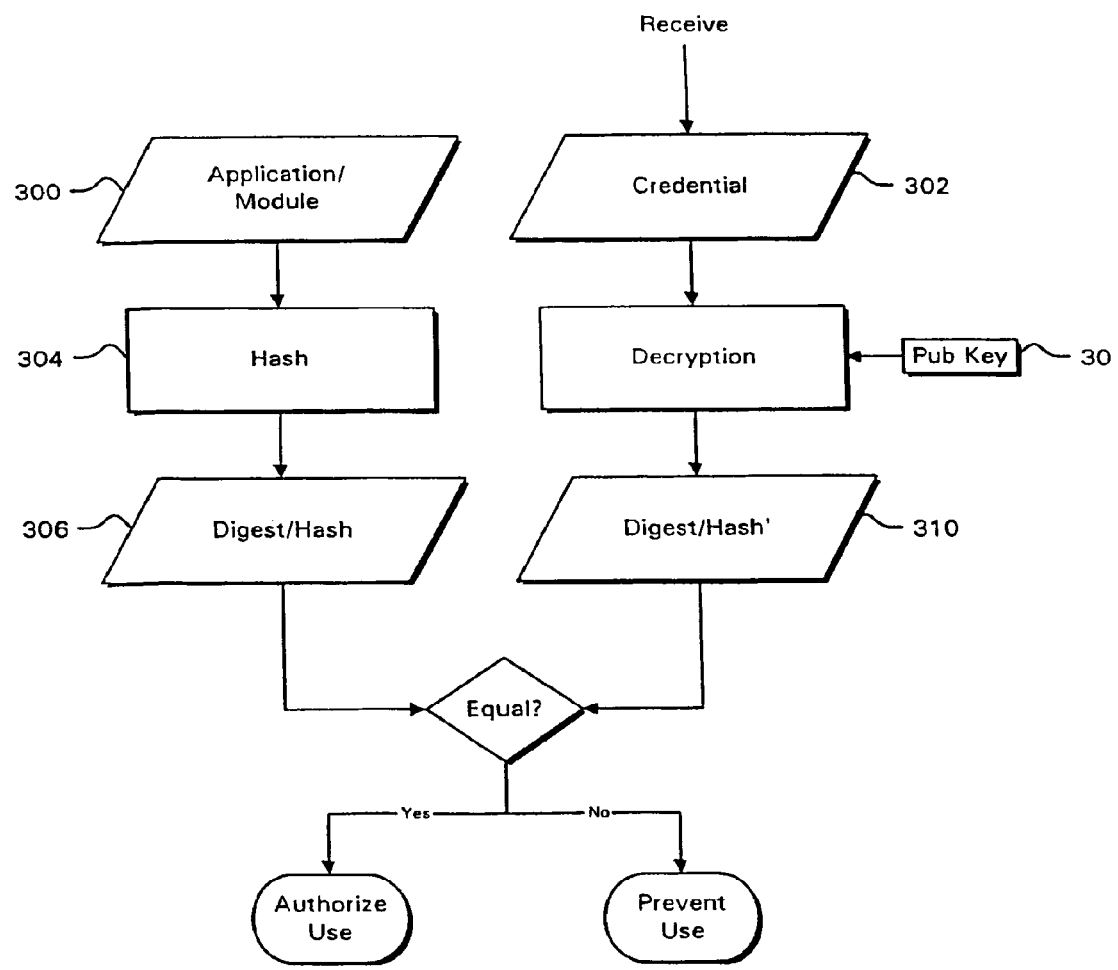

FIG. 3B illustrates a method by which the user's system can determine if a valid credential is associated with an application 300. Referring to FIG. 3B, the user's system (or the digital rights management system operating in connection therewith) retrieves a potential credential 302 from the application. For example, the credential may have a predefined name and may be stored in a predefined application module. If a credential with the appropriate name is not found in the predefined location, use of the content and/or application is prevented. If a credential is found, the user's system verifies the integrity/authenticity of the credential and/or the application. For example, if the credentialing process shown in FIG. 2 is used, the user's system (and/or digital rights management system) decrypts the credential 302 using the certification (or credentialing) authority's public key 308, yielding message digest 310. The user's system (or digital rights management system) also applies hash function 304 to the appropriate portions of the application program 300 to yield message digest 306. Message digest 306 is then compared with message digest 310. If the two message digests are equal, the user's system can be confident (within the security bounds of the signature scheme) that application 300 is the same as that certified by certification service 104, as any modifications an attacker may have made to the application (or to credential 302) would cause the comparison to fail. It will be appreciated that other suitable methods can be used for checking the credential(s) 105 of an application 107, and that the appropriate method will typically follow from that used to generate the credential by certification service 104.

FIG. 4 shows a system in which multiple credentialing authorities 402 work independently to certify an application 407 to their own specifications, and to provide application 407 with their own credentials 405. As shown in FIG. 4, several credential authorities 402a, 402b, 402c might contract with the same certification service 404a to certify an application on their behalf. Alternatively, a credential authority 402n may elect to contract with its own certification service 404b. As yet another option, certain credential authorities 402x may elect to perform the certification process themselves.

Similarly, multiple credential authorities 402a, 402n may arrange with the same packager 410b to prepare content and/or controls on their behalf. Alternatively, credentialing authorities 402a may arrange with their own dedicated content and/or controls packager 410a, or may perform these functions themselves (402x). Thus, content owners can choose to condition an application program's access to content on the application program's possession of a suitable combination of credentials, the credentials originating from a variety of credential authorities and/or certification services and attesting to the application's compliance with the authorities' specifications and requirements.

It can thus be seen that the systems and methods of the present invention enable a variety of certification and control arrangements to be put in place with relative ease. The controls that are associated with a particular piece of content can simply check for the presence of an entity's certification, and need not specify the very specific manner in which the content is to be, e.g., displayed or used, since this behavior is assured by the certification process. Such an approach also enables the certification process to be distributed and/or delegated across multiple, independently-responsible entities, thus obviating the need for a central entity to take each industry group's certification requirements, certify applications in accordance therewith, and stand behind the accuracy of the certification process. By allowing certification to be delegated, it is possible to obtain certifications more rapidly, to enable parties to certify applications themselves with whatever level of rigor they choose, and to allow the risk of improper certification to be borne by more than one party. Delegation and distribution of certification authority may also help create a market of certification providers, thus allowing content providers and credential authorities to benefit from efficiencies of scale, specialized certification experience, and market competition.

Delegation and decentralization of the certification/credentialing process also facilitates the creation of certain flexible models for sharing information. With a centralized system it may be infeasible or inefficient to express the very specific and idiosyncratic sorts of controls on, e.g., content presentation and manipulation that certain industry groups, content creators, governmental or regulatory bodies, or other organizations may want to specify in connection with the use of certain content.

For example, a pharmaceutical company might wish to require that content only be accessed by applications that display prescriptions in a certain font size. A music company might wish to require any device that allows access to the music company's content to display the music company's logo in a predefined manner. Given the wide variety of industries, and groups within each industry, each of whom might have its own specific rules regarding the use of certain content; it may be difficult for a single entity to certify that a variety of different applications meet the requirements specified by each industry group, and to provide the controls necessary for content providers to take advantage of those features. The systems and methods of the present invention avoid this problem by enabling application-specific content handling behavior to be controlled by a credential check, and by providing a decentralized mechanism for content owners or credentialing authorities to ensure, via the certification process—with whatever level of rigor is desired—that the presence of a valid credential can be relied upon as an effective assurance that content will be handled in the desired manner.

It will thus be appreciated that there are a variety of ways to advantageously apply the systems and methods of the present invention. Several exemplary applications are provided below for purposes of more clearly illustrating various aspects of the present invention.

Figure 5:
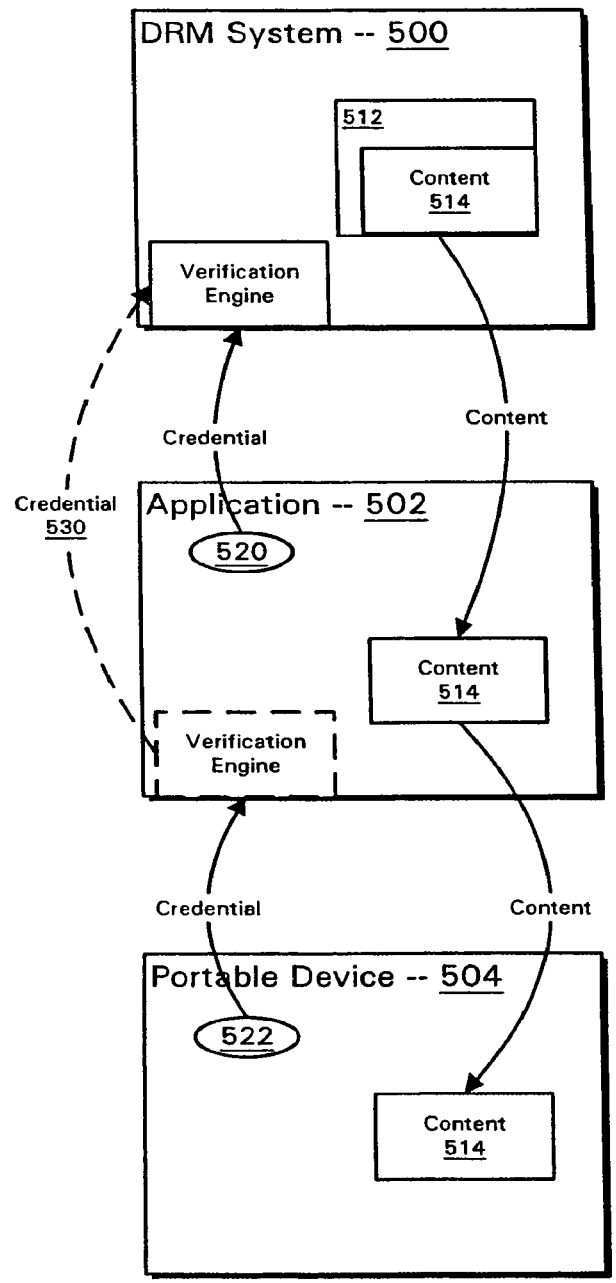
FIG. 5 illustrates an arrangement for managing electronic content in accordance with an embodiment of the present invention.

As shown in FIG. 5, in one embodiment credentialed applications are nested (or chained), such that one credentialed application is used to effectively control the use of content by other credentialed applications or devices. Referring to FIG. 5, a digital rights management system 500 is shown that contains an electronic content file 514 in its protected storage (or otherwise under its control—e.g., stored in unprotected storage but encrypted with a protected key). The file is packaged using the encoding format 512 of the digital rights management system 500, which may associate various rules and controls with the content to govern its use. One such control specifies that for an application 502 to gain access to content 514, the application must possess a predefined credential 520. Similarly, application 502 is operable to transmit a copy of content 514 to portable device 504 only if portable device 504 can produce a valid credential 522 (which application 502 may verify itself or pass to digital rights management system 500 for secure verification, as indicated by dotted line 530). Credentials 520 and 522 can be provided to application 502 and/or portable device 504 (e.g., stored in a predefined memory location) by appropriate credentialing authorities in the manner illustrated in FIGS. 1 and 4. For example, the issuance of a credential 520 to application 502 may be conditioned on a demonstration by application 502 that it can handle interactions with portable devices in an appropriate manner (e.g., certification of the application may be dependent on the application demonstrating that it will check the certification status of a portable device before transmitting protected content or keys to the portable device). Thus, digital rights management system 500 acts as the gatekeeper or root in a chain of interlocking credential checks. An arbitrary number of digital rights management systems, applications, and/or devices can be interlocked in this manner. If application 502's credential is revoked, application 502 may no longer be able to access encoded content 514 and pass it to portable device 504. Revocation can be accomplished by issuing credentials that expire, or simply by sending an updated control to digital rights management system 500 that effectively revokes recognition of the credential held by application 502.

It should be noted that the nesting properties described above are not limited to application programs and portable devices, but can also be applied to virtually any program, device, process, or entity. For example, in one embodiment multiple digital rights management systems can be chained in the manner described above. Such a process can be facilitated using the techniques described in commonly-assigned patent application Ser. No. 09/874,744, entitled "Systems and Methods for Governing Content Rendering, Protection, and Management Applications," filed Jun. 4, 2001, which is hereby incorporated by reference in its entirety.

In another exemplary embodiment, the digital rights management hardware and/or software on the user's system is operable to independently check connecting applications and devices for one or more credentials. That is, the digital rights management system may verify that an application meets certain requirements, regardless of whether the content owner packaged its content in a way that requested such a check to be performed. For example, in one preferred embodiment, applications are certified by the digital rights management provider to ensure that interoperable applications provide a basic level of trusted operation with respect to such fundamental content manipulation processes as copying, saving, moving, printing, and the like. The user's digital rights management software/hardware automatically checks for this basic certification when it is requested to send content to an application. Additional layers of certification—for example, industry-specific content presentation requirements—are only checked if the content packager explicitly asks for such checks to be performed. In other embodiments, such as in an enterprise setting, the user's digital rights management software/hardware may automatically check for a larger, more restrictive set of credentials, such as enterprise-specific credentials related to the types of operations that are authorized within the enterprise and/or by particular users within the enterprise. It will thus be appreciated that system architects and/or regulators (e.g., governments, industry groups, etc.) can set a certain baseline of credentials that must be present regardless of whether the content owners/packagers using the system specifically ask for such credentials to be present.

Alternatively, or in addition, in some embodiments credentials are issued to content packaging applications and securely associated with the packaged content. The user's digital rights management system and/or application software can check for the presence of the credential as a precondition for rendering the content. This type of credential would thus give system architects and/or application developers a level of control over the type of content used in their system or with their applications. For example, a school district, parents association, or regulatory body may wish to only allow use of educational content from certain pre-approved sources. The school district could issue a credential to those pre-approved sources which would be packaged with the content. The user's digital rights management software would check for the presence of the credential before sending the content to an approved application. If such an "approval" credential were to fall into the wrong hands, or if the credential owner failed to abide by the school's policies regarding what constitutes appropriate content, the credential could simply be revoked. A related example would be a hospital or pharmacy's requirement that all prescriptions received on its system originate from a properly-credentialed physician.

Moreover, content could be packaged in such a manner that it includes its own credential, while at the same time containing controls requiring checks to be performed for certain application credentials as a precondition for its use. Thus, the content's credential could be used by a system architect to screen unwanted content, while the application's credential could be used by the content owner to prevent use of the content on uncertified applications or devices.

In another exemplary embodiment, a credential might be used to certify that an application verifies (or purposely does not verify) the identity of its operator in a predefined fashion. Credentials could also be assigned to individual operators and/or systems upon the production of suitable identification, thus facilitating the secure transfer of content between particular credentialed users. User identification can be accomplished using digital certificates or credentials, or in any other suitable manner. For example, the user might establish his or her identity by using a password to log into the rights management system and/or the system on which the rights management system is installed. Once the identity of a user has been validated, this information can be used to control the transfer and/or packaging of content, access to applications, or any other suitable set of operations.

In some embodiments the credentials themselves may be interdependent. For example, one industry group may require as part of its certification procedure that an application first be credentialed by another industry group. If at any time the other industry group's credential were to expire or be revoked, any credentials that were effectively dependent on that credential would also cease to be valid.

In some embodiments, the rules associated with a piece of content may also contain instructions that can be passed to properly-credentialed applications. The credentialed applications would be operable to retrieve the instructions and use them to process the protected content in an appropriate manner. The digital rights management system that verified the presence and authenticity of the application credential need not be able to understand the instructions itself. This provides a way for one general-purpose digital rights management system to provide security and interoperability with other, application-specific digital rights management systems.

Figure 6:
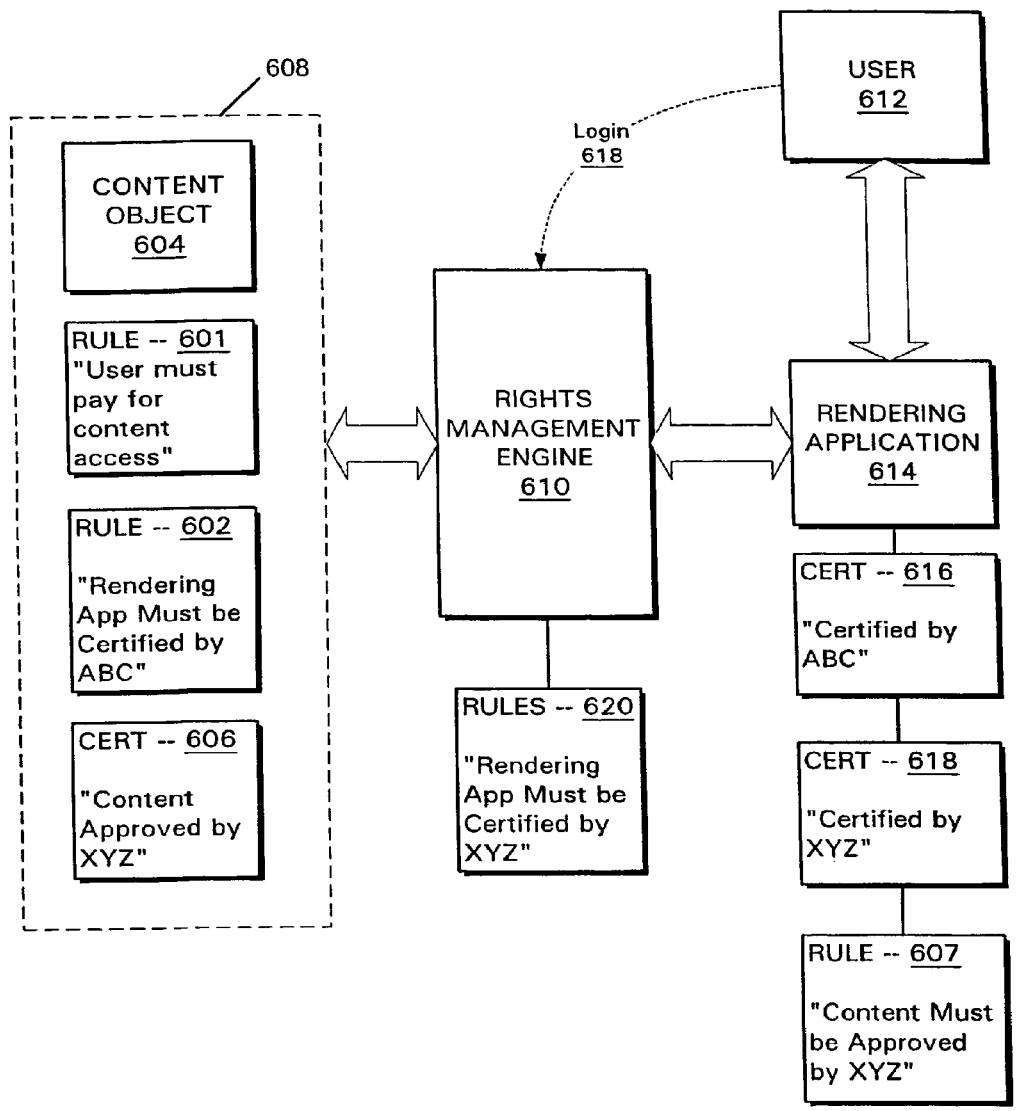
FIG. 6 illustrates another arrangement for managing electronic content and applications in accordance with an embodiment of the present invention.

FIG. 6 illustrates the use of credentials in accordance with embodiments of the present invention. Referring to FIG. 6, a user 612 uses a rendering application 614 to access content 604. Content 604 is securely packaged and associated with rules 601, 602 that govern how the content can be used. As shown in FIG. 6, rule 601 indicates that the user may access content object 604 if the user has purchased the rights to do so. Rule 602 indicates that in order for a rendering application to access content object 604, the rendering application must have been certified by an entity "ABC". For example, if content object 604 comprises a movie, song, book, or the like, entity ABC might represent the content's author, owner, or an industry association of content owners, and the certificate 616 specified by rule 602 may signify that rendering application 614 has been designed to operate in a manner that will safeguard the content owner's interests (e.g., by preventing copies of the decrypted content to be made.). Content object 604 is preferably protected (e.g., encrypted) such that rights management engine 610 controls access to it. For example, content object 604 might be encrypted using an encryption key held by the rights management engine in secure storage.

As shown in FIG. 6, content object 604 may also have a certificate 606 associated with it, the certificate indicating that another entity ("XYZ") has approved or otherwise certified content 606 as having certain predefined characteristics. For example, as previously described, if content object 604 comprises educational material, XYZ might be a regulatory authority responsible for evaluating the suitability of content 604 for a certain audience. Or, if content object 604 represented a prescription, certificate 606 may indicate that content object 604 originated from an approved source (e.g., a licensed physician or a certified packaging program).

As shown in FIG. 6, when a user 612 requests access to content 604 via a rendering application 614, the request is routed to the rights management engine 610. Rights management engine 610 detects the association between rules 601, 602 and content object 604, and evaluates whether the conditions specified by the rules have been satisfied. In the example shown in FIG. 6, the condition specified by rule 602 has been met, since rendering application 614 has a certificate 616 indicating that it has been approved by entity ABC.

Having determined that the rules 602 governing access to content 604 have been satisfied, rights management engine 610 may release content 604 to rendering application 614 (e.g., by decrypting it). Alternatively, digital rights management engine 610 may be programmed by the system operator (e.g., the school district, pharmacy, or other entity upon which the rendering application is loaded) to first determine whether the rendering application possesses yet another certificate 618, this certificate attesting to the application's conformance with another set of functional requirements specified by another entity (e.g., the school district, pharmacy, system operator, etc.). For example, it may be desirable to certify that application 614 will check content 604 for the appropriate certificate 606 before presenting the content to the user 612. Since the content owner may not care about this requirement, content 604 may not have been packaged with a rule indicating that such a check needs to be performed. Thus, to ensure that such a check is performed, system administrator might send an additional rule to the rights management engine 610 indicating that this check needs to be performed (i.e., that content 604 must have a certificate 606 indicating that content 604 has been approved by XYZ). It will be appreciated that this can be accomplished in any of a variety of ways. For example, a rule 607 could be delivered to rights management engine 610 indicating that only content that has a certificate 606 may be released to a rendering application 614. Alternatively, or in addition, a rule 620 can be delivered to rights management engine 610, the rule indicating that in order for a rendering application 614 to receive decrypted content, it must be certified by XYZ, certification by XYZ signifying that the application was designed to check for a certificate 606 before releasing content 604 to user 612 (e.g., by sending rule 607 to rights management engine 610). As yet another example, the system administrator could simply contract with the application developer to provide rendering applications that check for certificate 606, and only install such rendering applications on the system.

Thus, it will be appreciated that a number of modifications and variations can be made to the illustrative embodiment shown in FIG. 6 without departing from the present invention. For example, as shown in FIG. 6, in some embodiments, user 612 may be required to login to the rights management engine 610 (e.g., using a password, smartcard, biometric identification technique, or the like) and/or the system or systems on which rights management engine 610 and/or rendering application 614 are loaded. Moreover, in some embodiments, rules 602 might also have credentials attesting to their origin and/or approval by one or more entities, and applications 610, 614 may be operable to check for such credentials before applying these rules.

It should be appreciated that the system and relationships shown in FIG. 6 can be implemented in any suitable fashion. For example, rendering application 614, rights management engine 610, and content 604 may all be stored on the same system (e.g., in the memory of a personal computer), or may be distributed between multiple systems (e.g., rights management engine 610 and/or content 604 might be located on a system that is remote from the system on which rendering application 614 is running). Moreover, as shown in FIG. 6, content object 604, rules 602, and certificates 606 may be packaged together in a secure electronic container 608 that is accessible to the rights management engine 610. Alternatively, some or all of these objects may be packaged and/or delivered separately.

It should also be appreciated that while embodiments can advantageously be used in an environment in which each user's system includes relatively sophisticated digital rights management software for managing content in accordance with a variety of rules and controls, the systems and methods of the present invention can also be advantageously applied to environments in which the rights management software on the user's systems is relatively simple, and is operable to do little more than check for the presence of specified credentials. In such embodiments, while the foundational enforcement of the content owner's wishes can still be thought to reside in the user's rights management software—since it is responsible for checking applications for the requisite credentials and certifications and conditioning access to the content on the results of that process—the responsibility for the complex array of possible uses by the application is effectively enforced by the content owner and/or credentialing authority through the certification process (and the renewal, expiration, and/or revocation of credentials). Thus, while the rights management provider may be relied upon to provide a certain baseline of trust and security (with varying degrees of security and/or reliability, depending on its implementation), the complex interplay between application developers, content owners, and credential authorities can be delegated and decentralized, thus enabling faster adoption and modification of business arrangements between the potentially numerous parties involved, and more flexible, diverse, and narrowly-tailored content usage controls and requirements. Note however, that in some embodiments, a separate digital rights management system need not be used. Instead, the rights management functionality could simply be implemented directly by the application or a module thereof.

Figure 7:
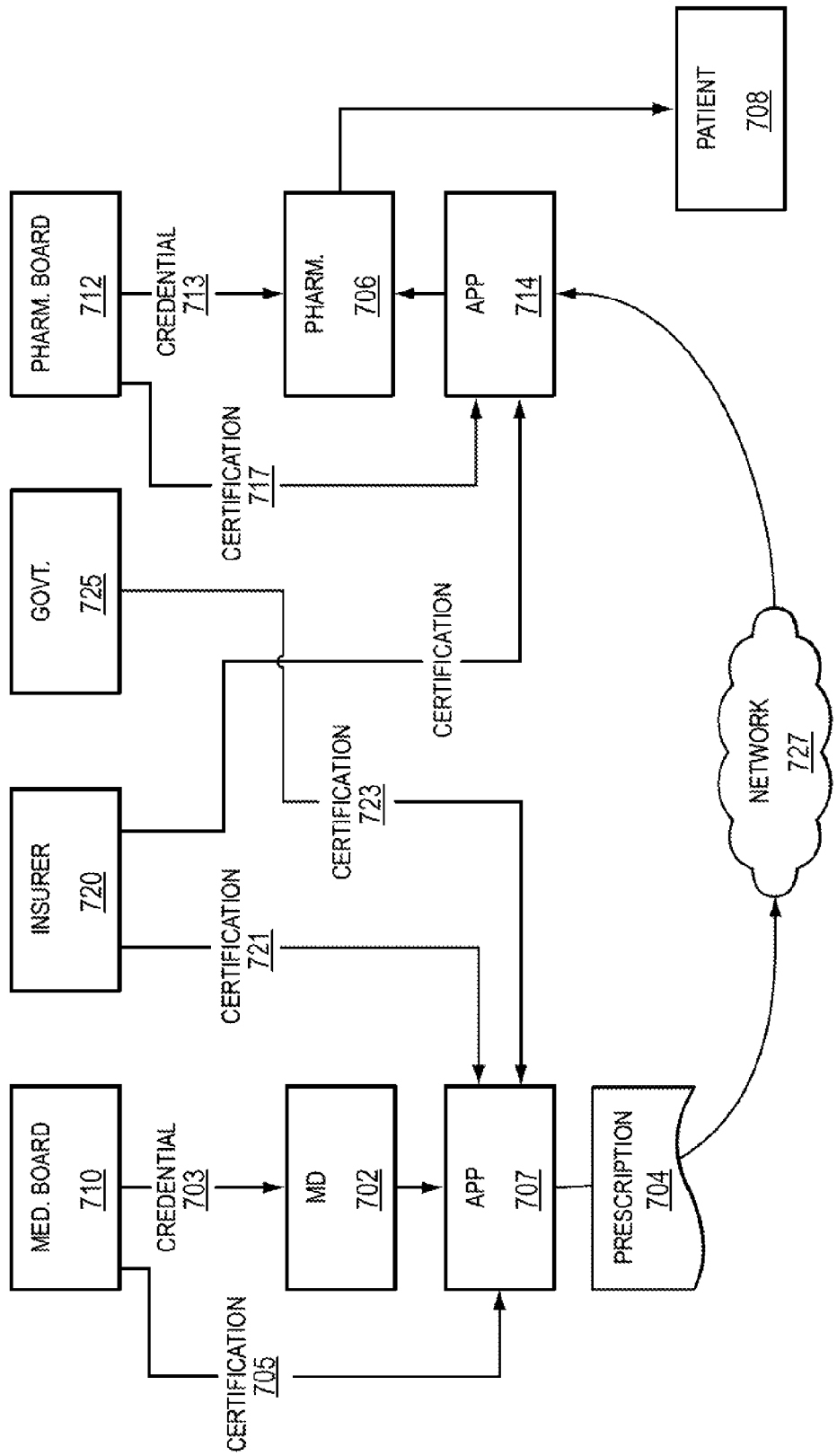
FIG. 7 illustrates a system for managing the generation and use of prescriptions in accordance with an embodiment of the present invention.

FIG. 7 illustrates the application of rights management techniques, such as those described above, to secure the functions/events related to prescribing medicine. In particular, FIG. 7 illustrates a system that enables prescriptions to be electronically generated and filled in a secure fashion.

As shown in FIG. 7, physicians 702 write prescriptions 704 using application programs 707, and transmit the prescriptions (or otherwise make the prescriptions available) to pharmacists 706 (e.g., via network 727). Pharmacists 706 fill the prescriptions and provide the prescribed medication to patients 708. Patients 708 and/or their insurers are then billed for the medication.

As shown in FIG. 7, rights management techniques can be used to control the integrity and efficiency of this process. For example, if it were desired to allow only a licensed physician to write prescriptions (or certain types of prescriptions), the prescription packaging application 707 could require physicians 702 to first present a valid credential 703 issued by a medical licensing authority 710, the credential identifying the physician as being licensed to issue prescriptions. The application may also require the physician 702 to login using a password, smartcard, or biometric information, and may also generate audit records regarding the physician's activities.

In addition, the packaging application 707 may itself be certified by the medical licensing authority 710. For example, the medical licensing authority 710 could codify its requirements for ensuring that only licensed physicians write (package) prescriptions, and provide these requirements to a certification agent, as described above in connection with FIG. 1. The prescription packaging application 707 would then be certified against these specifications. For example, the application 707 may receive certification 705 only if it is designed to check for the credentials of users/physicians in an appropriate manner. Prescriptions that are not generated by a certified application 707 could be identified and rejected by the other entities shown in FIG. 7, since such prescriptions may not have been generated by a licensed physician, or might be otherwise defective.

As shown in FIG. 7, a similar process can be used to ensure that only a licensed pharmacist 706 is able to fill a prescription. Licensed pharmacists 706 receive credentials 713 from a licensing authority 712. The pharmacist's application 714 and/or the digital rights management functionality incorporated therein, may also require users to log in using a password or other identification technique. Alternatively, or in addition, the pharmacist licensing authority could codify its requirements for prescription rendering application 714 and provide these requirements to a certification agent. The certification agent would issue credentials 717 to prescription rendering applications 714 that satisfied these requirements. Thus, to ensure that prescriptions are only accessed by licensed pharmacists, prescription packaging applications 707 could package prescriptions 704 in protected form, with an associated rule that required the detection of an appropriate credential or credentials (e.g., the credential of a licensed pharmacist and/or of an application that had been certified to detect such a credential) before allowing access to the prescription data.

Other entities may also wish to impose certain constraints on the physician and/or pharmacist. For example, an insurer 720 may wish to ensure that physicians prescribe generic medicine when it is as good as a brand name drug. In addition, the insurer or a governmental entity may also wish to ensure that any medicine that is prescribed does not conflict with previous prescriptions. To effectuate such control, the packaging application could be required to possess a certificate 721 from the insurer or its agents that confirmed that the packaging application had been designed in a manner that ensured that these functions would be performed (the functions themselves could be performed in any manner deemed suitable by the certifying authority). The system administrator could check for this credential (which would not necessarily need to be in electronic form) as a condition to installing the application on the system, and/or prescriptions packaged using such applications could indicate the certification status of the packaging application, thus allowing other system participants (e.g., pharmacists 706) to check for the presence of this credential as a condition of accepting a prescription.

It will thus be appreciated that any suitable combination of certificates can used to ensure that the system operates in the desired manner and that the rights and interests of the system participants are protected. For example, an insurer might certify the pharmacist's application only if it provides billing information in a particular manner, and pharmacists could be prevented from accessing prescriptions for a patient covered by the subject insurer without having the credential present that indicates the insurer or its delegated agent has certified the application. Similarly, the Federal government or a consumer watchdog group may issue certificates to applications that handle medical records in conformance with certain privacy requirements. In short, the present invention provides a flexible mechanism for managing the packaging and use of electronic data in a wide variety of ways and in accordance with the requirements and interests of a wide variety of disparate institutions. While several examples have been given in the context of medical or educational content, and content such as songs, movies, books and reports, one of skill in the art will recognize that these are but a few illustrative examples of the general applicability of the concepts presented herein.

As previously indicated, the credentials associated with an application can take a variety of forms and can be issued from any of a variety of entities. In some embodiments a credential may simply comprise a digital signature or other indication that an entity has generally approved the application, and/or confirmed that the application functions in a certain manner. In other embodiments, the credential may contain more detailed information, such as information regarding the level of security the application possesses, or other information that can be used to make decisions regarding the content the application is allowed to access and/or the operations the application is allowed to perform.

As described above, one way for content owners and/or application developers to control the risk that their property will be stolen or misused is by associating special rules with their content and/or applications. These rules can be used by a digital rights management system and/or rendering application to test for various attributes of the systems and/or applications upon which the content and/or applications are used. For example, rules associated with content and/or applications can be used to check for credentials that identify system characteristics such as:

Digital Rights Management System Attributes and Capabilities. The attributes and capabilities of the client-side digital rights management system can themselves be checked. For example, content use may be preconditioned on the existence of certain capabilities or protection mechanisms. The presence or absence of these capabilities could be provided in an credential stored by the digital rights management system, or could be obtained from the digital rights management system in some other fashion. For example attributes such as the following could be checked:

(a) Level of Tamper Resistance. The content provider may check whether the digital rights management system uses dedicated hardware tamper resistance (e.g., a secure processing unit); a mixture of hardware and software tamper resistance; or software tamper resistance only.

(b) Digital Rights Management Version. The content provider may only wish to allow access on a specific version of the digital rights management system.

(c) Operating System. The content provider may wish to allow only certain types of access on certain operating systems (e.g., Windows, Macintosh, Linux, etc.) or versions of operating systems (e.g., Windows 95, Windows 98, Windows NT, Windows 2000, Windows XP).

User Attributes. The content owner may also wish to check certain attributes or credentials associated with the user. For example, user authentication can be accomplished by creating a token during activation or as a result of subsequent interactions with the digital right management system's deployment manager and/or clearinghouse infrastructure. This token and its associated attributes (if any) can be checked by the client digital rights management software. For example, the tokens may be associated with some or all of the following attributes:

(a) Physical confirmation of identity
(b) Validated Name, Email, Address
(c) Unvalidated Name & Email
(d) Anonymous Application/Module Credential Attributes. Attributes of the applications used to render or process the content can also be checked. For example, some or all of the following types of attributes could be associated with an application, and included in control sets associated with the content:

(a) ID Attribute. Allows a control to check for a specific application or module ID. This can be used to restrict access to only certain applications, modules, or components.

(b) "Certified By" Attribute. Indicates who has certified the component for proper behavior and architecture. For example, this attribute may indicate that the application or module was certified by the provider of the trust management engine, or that the application or module was self-certified by the application or module developer.

(c) Content Exposure Attribute. Indicates the level of exposure within the module to unauthorized content use. The level of exposure will be directly related to the module's architecture and use of scripting, plug-ins, and so forth. Values for this attribute (set by, e.g., the digital rights management provider) might include:

(i) Minimal Exposure. No obvious attacks exist; only obscure attacks requiring sophisticated programming skills Dependent module credentials are fully checked.

(ii) Moderate Exposure. Known attacks exist, but require some programming skills Dependent modules may be checked. An example would be an application based on the COM architecture.

(iii) High Exposure. Known attacks exist, and are easily mounted using available tools and utilities and requiring little or no programming skills Dependent modules are typically not checked. An example would be an application with non-trusted scripting or add-in capabilities.

(d) Output Driver Attribute. Indicates whether the module checks output drivers for integrity (valid credential or signature). For example, this attribute might indicate that:

(i) Module implements a direct check of output driver credentials.

(ii) Module implements an indirect check of output driver integrity.

(iii) Module does not check output drivers.

(e) Output Device Attribute. Indicates whether the module checks output devices for integrity. For example, this attribute might indicate that:

(i) Module implements direct check of output device.

(ii) Module implement indirect check of output device.

(iii) Module does not check output devices.

FIG. 8 shows several credentials 802, 812 that include the attributes described above. Referring to FIG. 8, credential 802 illustrates a credential with multiple attributes that can be associated with the digital rights management application on a user's system. Credential 802 contains the digital signature 804 of its issuer (thus attesting to the authenticity of the credential and protecting against undetected modification), as well as fields that specify certain attributes of the local digital rights management system, such as its tamper resistance (806) and the platform on which it is installed (808). Credential 802 may also contain specify a variety of other attributes. Similarly, credential 812 illustrates a credential that might be associated with a content-rendering application. As shown in FIG. 8, credential 812 might include an attribute that indicates the level of content exposure associated with the application (814), an indication of whether the application checks output drivers for integrity (816), and the like. It should be appreciated that there are a wide variety of ways to implement the functionality described above. For example, the attributes shown in FIG. 8 as part of a single credential could, instead, be distributed across multiple credentials and/or additional attributes could be added to each credential.

When a digital rights management system obtains a piece of content that requires that certain ones of these attributes be satisfied, it can retrieve credential 804, verify its signature, and check the values of the appropriate attributes to see if the conditions are satisfied, in which case the desired use of the content can be allowed.

The provider of the digital rights management system (or other secure client software), may issue a credential to applications certified by the provider as meeting certain security requirements. A lesser level of "certification" may be provided to applications that are merely capable of operating in connection with the secure processing software, but about which the provider makes no representations as to security. These different levels of certification could be represented by different credentials assigned to the application, or by different attributes specified in a single credential.

As described elsewhere herein, specific industries or associations may elect to define attributes or certificates to indicate that the application meets the required industry or association requirements for capability, security, privacy, etc. These attributes may also be checked by controls to ensure that content is only accessible to approved applications. For example, a national medical association may wish to define an attribute that indicates that an application meets the association's guidelines for handling of patient medical data. As another example, a privacy certification provider may wish to define an attribute that indicates the application meets its guidelines.

This approach implies the existence of more than one agency involved in setting credential attributes based on their own independent testing. Each agency would be responsible for securely adding the agency's attribute to an existing credential. In one embodiment, the application writer would submit the application to one agency for certification, and then take the application and the credential from the first agency to other agencies for additional certification.

Since there are many reasons a user may not be able to access a specific piece of content with a given application, the application should be capable of displaying a reasonable message to the user that describes why they can't access the content. For example, if an application does not support the format or version of the requested content, a message such as "This application does not support the requested data type (mime type)" could be displayed. If the control requires a membership card which does not exist, has expired, etc., an error message such as "No valid controls/offers exist for this content. Contact <control provider name>" could be provided. Similarly, if the control requires application credential attributes that are not set, a message such as "This application is not authorized for this content. Contact <application provider>" could be displayed. As yet another example, if a user does not have the required authentication level, a message such as "Your account is not authorized for this content. Contact <authentication level provider>" could be displayed.

Figure 9:
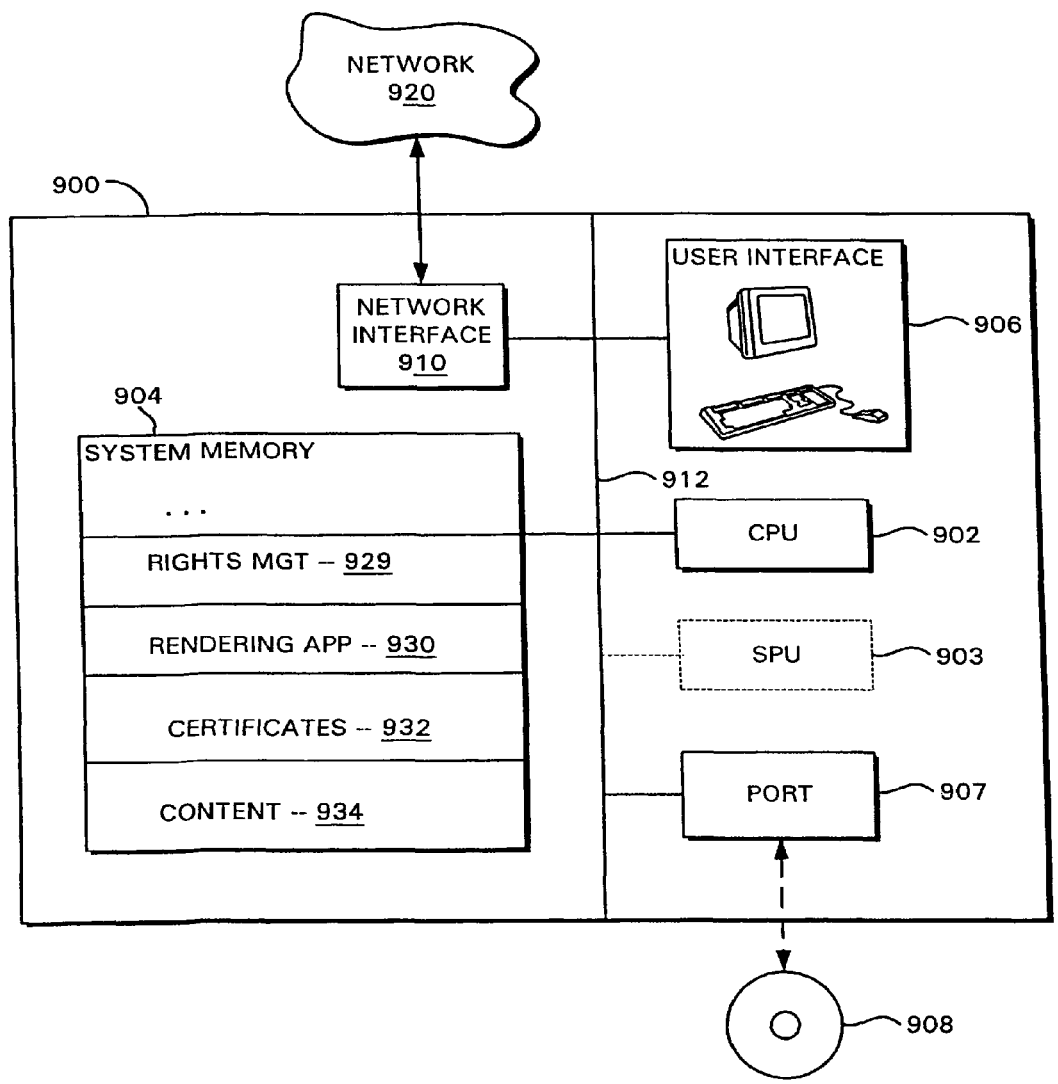
FIG. 9 illustrates a computer system for practicing embodiments of the present invention.

FIG. 9 shows an example of a computer system 900 that can be used to practice embodiments of the present invention. Computer system 900 may comprise a general-purpose computing device such as a personal computer or network server, or a specialized computing device such as a cellular telephone, personal digital assistant, portable audio or video player, television set-top box, kiosk, or the like. Computing device 900 will typically include a processor 902, memory 904, a user interface 906, a port 907 for accepting removable memory 908, a network interface 910, and a bus 912 for connecting the aforementioned elements. The operation of computing device 900 will typically be controlled by processor 902 operating under the guidance of programs stored in memory 904. Memory 904 will generally include both high-speed random-access memory (RAM) and non-volatile memory such as a magnetic disk and/or flash EEPROM. Some portions of memory 904 may be restricted, such that they cannot be read from or written to by other components of the computing device 900. Port 907 may comprise a disk drive or memory slot for accepting computer-readable media such as floppy diskettes, CD-ROMs, DVDs, memory cards, other magnetic or optical media, or the like. Network interface 910 is typically operable to provide a connection between computing device 900 and other computing devices (and/or networks of computing devices) via a network 920 such as the Internet or an intranet (e.g., a LAN, WAN, VPN, etc.). In some embodiments, computing device 900 includes a secure processing unit 903 such as that described in the '900 patent. A secure processing unit can help enhance the security of sensitive operations such as key management, signature verification, and other aspects of the rights management process.

As shown in FIG. 9, memory 904 of computing device 900 may include a variety of programs or modules for controlling the operation of computing device 900. For example, memory 904 will typically include one or more content rendering applications 930 (such as document editors or viewers, electronic book readers, video players, music players, electronic mail or messaging programs, or the like) for presenting electronic content to users of the system. In some embodiments, one or more of the rendering applications 930 may also be capable of applying policies, rules, and/or controls to govern the use of content or the performance of events. Alternatively, or in addition, these policies, rules, and/or controls may be applied by a rights management program 929 such as that described above and/or in the '900 patent. Memory 904 may also include a program—such as that described in U.S. patent application Ser. No. 09/617,148, entitled "Trusted Storage Systems and Methods", filed Jul. 17, 2000, which is hereby incorporated by reference—for maintaining a database of protected data, such as cryptographic keys, certificates, or the like. In addition, memory 904 will typically contain one or more pieces of protected content 934.

One of ordinary skill in the art will appreciate that the systems and methods of the present invention can be practiced with computing devices similar or identical to that illustrated in FIG. 9, or with virtually any other suitable computing device, including computing devices that do not possess some of the components shown in FIG. 9 and/or computing devices that possess other components that are not shown. Thus it should be appreciated that FIG. 9 is provided for purposes of illustration and not limitation as to the scope of the invention.

Although the foregoing invention has been described in some detail for purposes of clarity, it will be apparent that certain changes and modifications may be practiced within the scope of the appended claims. It should be noted that there are many alternative ways of implementing both the processes and apparatuses of the present invention. Accordingly, the present embodiments are to be considered as illustrative and not restrictive, and the invention is not to be limited to the details given herein, but may be modified within the scope and equivalents of the appended claims.

What is claimed is:

1. A method for managing the use of protected electronic content by a rights management application executing on a computing device, the method comprising:
   receiving, from a first application executing on the computing device, by a second application executing on the computing device, a request to use the protected electronic content and a first credential associated with the first application;
   receiving, from the second application executing on the computing device by the rights management application, the request to use the protected content and a second credential associated with the second application;
   validating, by the rights management application, the second credential;
   sending, by the rights management application based on validating the second credential, the protected electronic content to the second application;
   validating, by the second application, the first credential; and
   sending, by the second application based on validating the first credential, the protected electronic content to the first application for use in accordance with the request.

2. The method of claim 1, wherein the first credential comprises a credential issued by a credentialing authority based on the credentialing authority validating that the first application meets a predefined level of security.

3. The method of claim 1, wherein the second credential comprises a credential issued by a credentialing authority based on the credentialing authority validating that the second application meets a predefined level of security.

4. The method of claim 1, wherein the request to use the protected electronic content comprises a request to render the protected electronic content.

5. The method of claim 1, wherein the request to use the protected electronic content comprises a request to receive a copy of the protected electronic content.

6. The method of claim 1, wherein the protected electronic content comprises electronic content stored in a protected storage managed by the rights management application.

7. The method of claim 1, wherein the protected electronic content comprises electronic content stored in unprotected storage encrypted with a protected key.

8. The method of claim 1, wherein the protected electronic content is associated with at least one control governing use of the protected electronic content.

9. The method of claim 8, wherein the at least one control requires possession of the first credential prior to allowing use of the protected electronic content.

10. The method of claim 9, wherein the at least one control is securely associated with the protected electronic content.

11. A non-transitory computer-readable storage medium storing instructions that, when executing by a processor of a computing system, are configured to cause the processor to:
   receive, from a first application executing on the computing system by a second application executing on the computing system, a request to use a piece of electronic content managed by a rights management application executing on the computing system and first credential associated with the first application;
   receive, from the second application executing on the computing device by the rights management application, the request to use the protected content and a second credential associated with the second application;
   validate, by the rights management application, the second credential;
   send, by the rights management application based on validating the second credential, the protected electronic content to the second application;
   validate, by the second application, the first credential; and
   send, by the second application based on validating the first credential, the protected electronic content to the first application for use in accordance with the request.

12. The non-transitory computer-readable storage medium of claim 11, wherein the first credential comprises a credential issued by a credentialing authority based on the credentialing authority validating that the first application meets a predefined level of security.

13. The non-transitory computer-readable storage medium of claim 11, wherein the second credential comprises a credential issued by a credentialing authority based on the credentialing authority validating that the second application meets a predefined level of security.

14. The non-transitory computer-readable storage medium of claim 11, wherein the request to use the protected electronic content comprises a request to render the protected electronic content.

15. The non-transitory computer-readable storage medium of claim 11, wherein the request to use the protected electronic content comprises a request to receive a copy of the protected electronic content.

16. The non-transitory computer-readable storage medium of claim 11, wherein the protected electronic content comprises electronic content stored in a protected storage managed by the rights management application.

17. The non-transitory computer-readable storage medium of claim 11, wherein the protected electronic content comprises electronic content stored in unprotected storage encrypted with a protected key.

18. The non-transitory computer-readable storage medium of claim 11, wherein the protected electronic content is associated with at least one control governing use of the protected electronic content.

19. The non-transitory computer-readable storage medium of claim 18, wherein the at least one control requires possession of the first credential prior to allowing use of the protected electronic content.

20. The non-transitory computer-readable storage medium of claim 19, wherein the at least one control is securely associated with the protected electronic content.

* * * * *